United States Patent [19]

Leir et al.

[11] 4,301,289
[45] Nov. 17, 1981

[54] PROCESS FOR 6,7-DIHYDRO-9-FLUORO-5-METHYL-1-OXO-1H,5H-BENZO(IJ)QUINOLIZINE-2-CARBOXYLIC ACID

[75] Inventors: Charles M. Leir, New Richmond, Wis.; Kirk G. Hedberg, Minneapolis, Minn.

[73] Assignee: Minnesota Mining and Manufacturing Company, St. Paul, Minn.

[21] Appl. No.: 122,657

[22] Filed: Feb. 19, 1980

[51] Int. Cl.$^3$ .................. C07D 455/04; C07D 215/22
[52] U.S. Cl. ........................................ 546/94; 546/153
[58] Field of Search ............................. 546/153, 94

[56] References Cited

U.S. PATENT DOCUMENTS 3,896,131  7/1975  Gerster ............................. 546/94

OTHER PUBLICATIONS

Jones, et al., J. Chem. Soc. Trans. 97, pp. 632-644 (1910).
Elderfield, et al., J. Am. Chem. Soc., vol. 71, pp. 1906-1911 (1949).
Mirek, Chemical Abstracts, 62, 5252b (1965).
Palmer, The Structure and Reactions of Heterocyclic Compounds, Edwin Arnold, Ltd., London, (1967), pp. 110-111.

*Primary Examiner*—Donald G. Daus
*Assistant Examiner*—Diana G. Rivers
*Attorney, Agent, or Firm*—Cruzan Alexander; Donald M. Sell; Carolyn A. Bates

[57] ABSTRACT

An improved process for preparing the antimicrobial compound flumequine is disclosed. The first step of the process comprises reacting 4-fluoroaniline with crotonaldehyde under acidic conditions at a temperature between 50° and 60° C. In the second step, the product of the first step is treated to provide a mixture of 6-fluoroquinaldine and 6-fluorotetrahydroquinaldine. This mixture is then treated with base in the presence of weak acid followed by reducing to provide 6-fluorotetrahydroquinaldine. This compound is then treated according to known procedures to form flumequine.

6 Claims, No Drawings

PROCESS FOR 6,7-DIHYDRO-9-FLUORO-5-METHYL-1-OXO-1H,5H-BENZO(IJ)QUINOLIZINE-2-CARBOXYLIC ACID

This invention relates to an improved process for the preparation of 6,7-dihydro-9-fluoro-5-methyl-1-oxo-1H,5H-benzo-[ij]quinolizine-2-carboxylic acid (flumequine) and intermediates therefor starting with 4-fluoroaniline.

Flumequine is a known antimicrobial compound described and claimed in U.S. Pat. No. 3,896,131 (Example 3). The starting material for the process described in that patent is 6-fluoro-2-methyltetrahydroquinoline (6-fluorotetrahydroquinaldine). 6-Fluorotetrahydroquinaldine is prepared from 6-fluoroquinaldine, a compound first described by Mirek (Chem. Abs. 62, 5252, 1965), by routine chemical or catalytic reduction procedures. The Mirek process for preparing 6-fluoroquinaldine involves treating 4-fluoroaniline with concentrated acid, zinc chloride and paraldehyde. The mixture is left at ambient temperature for two hours, followed by boiling, alkalization and steam distillation. The distillate is extracted with benzene, dried and the solvent removed. The residue is distilled in vacuo and dissolved in concentrated hydrochloric acid in water. The solution is treated with zinc chloride in hydrochloric acid and cooled. The precipitate is washed with cold hydrochloric acid, dissociated with concentrated sodium hydroxide and steam distilled to prepare 6-fluoroquinaldine. The yield of 6-fluoroquinaldine from the Mirek process is reported to be only 36.9%. When the 6-fluoroquinaldine is reduced to 6-fluorotetrahydroquinaldine in order to prepare flumequine an even further reduction in overall yield results.

The process of the present invention is a marked improvement over the prior art process. It results in significantly higher yields of 6-fluorotetrahydroquinaldine in the range of 70 to 80 percent. Furthermore, it offers various practical advantages including a reduction in the number of reagents and the number and difficulty of operational steps.

The present invention provides a process for preparing the compound 6,7-dihydro-9-fluoro-5-methyl-1-oxo-1H-5H-benzo[ij]quinolizine-2-carboxylic acid (flumequine) of Formula I

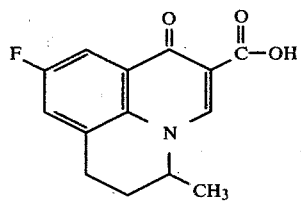

Formula I which comprises:
(1) reacting 4-fluoroaniline with crotonaldehyde, or a precursor for crotonaldehyde which generates crotonaldehyde under the acidic conditions of the reaction such as acetaldehyde, acetal or paraldehyde, optionally in an alcoholic solution, in the presence of dilute aqueous acid such as hydrochloric acid at a temperature between about 50° and 60° C. to provide the compound

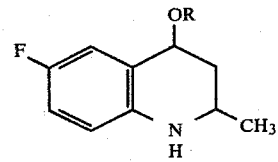

Formula II wherein R is hydrogen or alkyl having one, two or three carbon atoms, as e.g., the acid addition salts;

(2) heating the product of step 1) to provide a mixture of 6-fluoroquinaldine and 6-fluorotetrahydroquinaldine as the acid salts;

(3) treating the acid salts with base in the presence of weak acid following by reducing the mixture to provide 6-fluorotetrahydroquinaldine, optionally purified as the acid salt;

(4) condensing with a dialkyl alkoxymethylenemalonate (alkyl meaning one to three carbon atoms) such as the diethyl ester to provide the compound

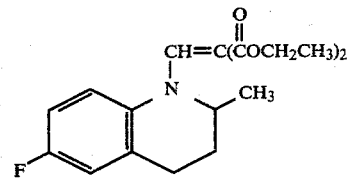

(5) cyclizing by heating in the presence of polyphosphoric acid and then saponifying to provide flumequine.

The novel intermediates of the invention are the compounds of Formula II, with compounds wherein R is hydrogen or methyl, especially as the hydrochloride salt, being preferred.

The essence of the invention lies in the first two steps of the process which are responsible for the significant increase in overall yield. In the first step of the preferred embodiment of the process, a slight e.g., 5% molar excess of an aqueous alcoholic (preferably aqueous methanolic) solution of crotonaldehyde is added to a mixture of 4-fluoroaniline and dilute hydrochloric acid. Paraldehyde can be used, but the yields and purity of the product are both poorer. Other reactants such as acetaldehyde, acetal and the like which are crotonaldehyde precursors under acidic reaction conditions may also be used. Pure crotonaldehyde or an aqueous solution of crotonaldehyde (e.g. 85%) can be used, but an aqueous alcoholic solution is preferred to maintain reaction homogeneity and increase yield. The ratio of methanol to 85% crotonaldehyde solution is about 1 ml per gram. The rate of addition of the aldehyde appears to have some effect on yield. Slow addition provides better yields of product. The rate of addition is somewhat easier to control using a solution of crotonaldehyde. In a 40 mole scale run, addition is desirably carried out over about 8 hours at a temperature of between about 50° and 60° C. and preferably at about 55° C. Careful control of temperature is very important since significant deviations from this temperature range result in a reduced yield.

It has been found that dilute hydrochloric acid, e.g. 2 to 6 N, preferably about 4 N gives the highest yields of product. The amount of hydrochloric acid used is about 0.5 liter per mole of 4-fluoroaniline. Other strong acids such as sulfuric or phosphoric acid may also be used.

In the second step of the reaction, the mixture from step one is optionally filtered to remove any solid contaminants, then heated to reflux to convert the compounds of Formula II to a mixture of 6-fluoroquinaldine and 6-fluorotetrahydroquinaldine. The presently preferred method of carrying out the heating step is disclosed and claimed in copending application Ser. No. 122,599 filed on even date herewith and comprises the slow addition of the filtrate to refluxing toluene and allowing the water to azeotrope out of the reaction mixture. In this way the product is obtained as the solid hydrochloride salts which are easily collected e.g., by filtration, and air-dried. Other azeotropes having a boiling point between about 90° and 120° C. such as water-acetic acid can also be used, but toluene is preferred since a solid product is formed.

Alternatively, the reaction mixture of step one may be heated as is under reflux, or toluene may be added and then the mixture refluxed. The product mixture is then isolated after discarding the organic phase, by basifying, extracting (e.g., with toluene), drying, and precipitating as the salts by adding acid (e.g., by bubbling in gaseous HCl). Optionally, after extraction and drying, the solvent (e.g., toluene) is removed in vacuo, a second solvent (e.g., acetone) is added, and the product precipitated as the salts by adding an acid.

For the reduction of step three, the dry solid is dissolved in a warm solution of isopropanol (about 1 ml per gram) and a weak acid such as acetic acid (about 1.0 ml per gram) and treated with a slight molar excess of a base such as ammonium acetate or triethylamine.

The mixture is cooled and the solid residue (ammonium chloride or triethylamine hydrochloride) is removed e.g., by filtration. To the filtrate is added a platinum-based reducing catalyst such as 5% platinum on carbon, about 10 to 20 g per mole, and the mixture is hydrogenated at a pressure of about 30 to 70 psi at a temperature of 15° C. or less. The progress of the reaction is readily monitored by chromatographic analysis. After completion of the reduction, the catalyst and other residual solids are removed by filtration. The solvent is removed by evaporation and the residue is dissolved in a suitable solvent such as isopropanol. The solution is treated with anhydrous acid such as hydrogen chloride to precipitate 6-fluorotetrahydroquinaldine as the acid salt. Overall yields are typically 70 to 85% of this first crop. Further product is obtained by concentration of the isopropanol solution to increase the yield by 5 to 10%.

Alternatively, after reduction, filtration and evaporation, the product is isolated as the free base, e.g., by suspending in water and neutralizing with weak base such as aqueous ammonia. Extraction (e.g., with toluene) followed by drying and evaporation provides 6-fluorotetrahydroquinaldine. This product may be further purified by vacuum distillation if desired.

In the fourth step, condensation of 6-fluorotetrahydroquinaldine with a dialkyl diester of ethoxymethylenemalonate such as the diethyl ester is carried out by heating the reactants without solvent at 100° to 200° C. for about 1 to 5 hours or until the reaction is complete. The intermediate is an oil which need not be isolated or purified.

To carry out step five, polyphosphoric acid is added to the oil from step four and the solution (optionally diluted with toluene) is heated at 100° to 140° C. to effect cyclization to the ester of flumequine. The ester is hydrolyzed to the free acid by adding water followed by heating at reflux under the acid conditions. The isolation and purification of flumequine can be completed e.g., by filtering to separate the solid product, followed by dissolving in sodium hydroxide solution and then precipitation with hydrochloric acid. The free base is optionally recrystallized from N,N-dimethylformamide.

The invention may be further illustrated by the following non-limiting examples.

EXAMPLE 1

To a 10 gallon glass-lined Pfaudler reactor were added 20 liters of 4 N hydrochloric acid, followed by 4-fluoroaniline (4,444.8 g, 40 moles). The mixture was heated to 55° C., and crotonaldehyde (3.463 g 85% aqueous soln., 42 moles) in methanol (3 liters) was added over 8 hrs. After the addition, the mixture was cooled to 20° C. and stirred overnight. The aqueous solution was pressure filtered through a 10 micron string filter, which was rinsed with 2 liters of water. Total volume of the solution was about 31 liters. The reactor was rinsed with water and acetone and dried with nitrogen. Toluene (20 liters) was added and brought to reflux (111° C.). The above aqueous solution was slowly added to the refluxing toluene, and the water resulting from the azeotrope was collected. Total time of addition was 5.7 hrs. The pot temperature decreased to 85° C. and stayed there during the first 6.7 hours of azeotroping. After this time, the mixture was cooled to 20° C. and stirred overnight. The next morning, a solid precipitate was noted in the reaction vessel. The azeotrope was continued. After 4.5 hrs., pot temperature had slowly risen from 87° C. to 100° C. After an additional 0.5 hrs., pot temperature was steady at 111° C. and there was no visible azeotrope being formed. After an additional 0.5 hrs., the reaction mixture was cooled to 25° C.

The solid was collected by filtration and rinsed with toluene (about 11 liters). The solid was sucked dry on a Buchner funnel for 22 hrs., followed by air drying an additional 42 hrs., yielding 7,535 g (93.5%) light brown solid. The solid was added to the dried 10 gallon reactor, alone with isopropanol (8 liters) and acetic acid (6 liters). The mixture was stirred and heated to 70° C., followed by the addition of ammonium acetate (3,084 g, 40 moles). The mixture was stirred 15 minutes at 70°-75° C., cooled to 20° C. for 0.5 hr., and filtered. The reactor and filter cake were rinsed with isopropanol (4 liters). The white solid was air-dried to give ammonium chloride (1,904.7 g, 89% recovery based on the ammonium acetate added). The solution was then hydrogenated in the clean, dry 10 gallon reactor, using 5% platinum on carbon (640 g, 50% w/w). The temperature was kept at 15° C. and hydrogen applied at 50 psi until hydrogen uptake ceased (about 20 hours).

The reaction mixture was filtered (3 micron string filter), and rinsed with isopropanol (about 4 liters). The solution was re-added to the cleaned 10 gallon reactor and the solvent removed in vacuo. (70°, 27.5 inches vac). The resulting dark oil was redissolved in isopropanol (8 liters) and the solvent removed in vacuo to remove residual acetic acid. The residue was allowed to cool to 20° C., dissolved in isopropanol (10 liters) and stirred overnight. This filtered solution was then added slowly (over 2½ hrs.) to a solution of hydrogen chloride gas (1.75 kg, 48 moles) in isopropanol (16 liters). The resulting slurry was cooled to 12° C., filtered, and rinsed twice with cold isopropanol (4 liters and 2 liters, respectively). The off-white solid was dried under vacuum (27 in) at 65° for 24 hrs., yielding 6-fluorotetrahydroquinaldine hydrochloride (5,857.5 g, 72.7%).

The mother liquors were concentrated in vacuo, redissolved in 2 liters of hot isopropanol, cooled overnight, and the mixture filtered. The resulting dark solid was stirred with 1 liter of hot isopropanol, cooled, filtered and rinsed with isopropanol. The resulting off-white solid was dried, yielding 6-fluorotetrahydroquinaldine hydrochloride (254.0 g, 3.2%).

The resulting mother liquors were concentrated in vacuo to 1,380 g dark oil. Analysis showed this was about 14% product, or 193 g, an additional 2.5% of product.

EXAMPLE 2

Crotonaldehyde (93%, 79.13 g, 1.05 moles) in methanol (75 ml) was added to a solution of 4-fluoroaniline (111.12 g, 1 mole) in 4 N hydrochloric acid (500 ml) over 3½ hrs., at 55° C.±5°. On completion of the addition, toluene (400 ml) was added, and the mixture was heated under reflux for 4 hrs. The mixture was cooled and the organic phase was discarded. The aqueous layer was basified with 50% sodium hydroxide solution (100 ml), to pH 11 and the liberated bases were extracted twice with toluene (400 ml and 200 ml, respectively). The combined toluene extracts were washed (300 ml) and the toluene solution dried by azeotropic distillation. Toluene was removed by distillation, acetone (300 ml) was added, and the solution was cooled to below 20° C. This solution was treated with hydrogen chloride (36 g), keeping the temperature below 35° C. until it was acidic. After cooling the suspension at 0° C. for two hours, the product was collected, washed with acetone (200 ml) and dried in vacuo at 35° C. to give a light brown solid. The mixture of hydrochlorides was isolated in 82% yield.

The mixture of hydrochlorides was suspended in acetic acid (50 ml) and isopropanol (100 ml) and heated with ammonium acetate (20 g) at 60° C. for 10 minutes. The precipitated ammonium chloride was removed by filtration and washed with isopropanol (25 ml). The filtrate was hydrogenated in the presence of 5% platinum on carbon catalyst (50% damp, 2 g) at an initial pressure of 60 psi.

Reaction was complete in 8–12 hrs. The catalyst was removed and the isopropanol in the filtrate was removed by evaporation.

Water (200 ml) was added, with cooling, and the solution was basified with ammonia solution (50 ml) to pH 9. The cooled solution was extracted twice with toluene (200 ml and 100 ml, respectively) and the combined organic layers were washed with water (300 ml). Finally, the toluene solution was dried by azeotropic distillation and the toluene was removed by evaporation under reduced pressure to give a dark brown oil which crystallized upon standing. Yield was about 93% of 6-fluorotetrahydroquinaldine. The yield was 76% overall.

EXAMPLE 3

6-Fluorotetrahydroquinaldine (12.05 kg containing 10% of toluene) and diethyl ethoxymethylene malonate (16.2 kg) were charged to a 225 liter Pfaudler reactor and heated at 125° C. under vacuum for 4 hours. Ethanol (3.1 kg) was recovered. The product was cooled, diluted with toluene (35 liters) and tetraphosphoric acid (35 kg), reheated to reflux for 2 hours, cooled to 80° C., diluted with water (128 liters) and refluxed for 6 hours to complete the hydrolysis. The crude flumequine was collected, washed acid free with water and rinsed with methanol. The damp cake was dissolved in sodium hydroxide solution (2.94 kg/59 liters) filtered hot through a cartridge filter heated to 90° C. and acidified with hydrochloric acid (6.64 liters). The product was collected, washed acid free, rinsed with methanol and dried in a vacuum oven. The yield of flumequine was 15.4 kg (90.8%). The dry solid was dissolved in N,N-dimethylformamide (70 liters) at 125° C., allowed to cool with stirring to 100° C. then cooled to 7° C. with cold water. The product was collected, washed with methanol and dried as before. The yield of recrystallized flumequine was 14.4 kg (82.3%) overall.

EXAMPLE 4

A mixture of 606 kg of diethyl ethoxymethylenemalonate and 400 kg of 6-fluorotetrahydroquinaldine was stirred and heated at about 125° C. for 5 hours. The mixture was cooled to about 95° C. and evaporated.

To the stirred reaction mixture was added 450 liters of toluene, then 908 kg of polyphosphoric acid at a rate to maintain a reaction temperature of 90° to 100° C. The mixture was then heated at reflux for fourteen hours.

To this mixture was added 950 liters of water over five hours. The ester was saponified by heating for 13 hours at 110° to 115° C. while removing the toluene via the toluene-water ezeotrope. The solid product flumequine was separated by filtration, washed thrice with hot water, then with N,N-dimethylformamide. Recrystallization form N,N-dimethylformamide gave white solid flumequine.

Alternatively, the water-washed flumequine was treated with ammonium hydroxide to dissolve it, decolorized, filtered, and then precipitated with concentrated hydrochloric acid. Recrystallization provided white solid flumequine.

What is claimed is:

1. A process for the preparation of flumequine comprising:

a. reacting 4-fluoroaniline with a reactant selected from the group consisting of crotonaldehyde, a precursor for crotonaldehyde which generates crotonaldehyde under acidic conditions, and an alcoholic solution of crotonaldehyde or said precursor for crotonaldehyde in the presence of dilute aqueous acid between about 50° and 60° C. to provide a compound of the formula

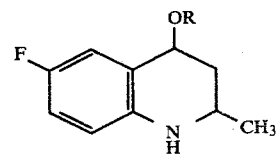

wherein R is hydrogen or alkyl having one, two or three carbon atoms;

b. heating the product of step (a) to provide a mixture of 6-fluoroquinaldine and 6-fluorotetrahydroquinaldine as acid salts;

c. treating said acid salts with base in the presence of weak acid followed by reducing the mixture to provide 6-fluorotetrahydroquinaldine;

d. condensing said 6-fluorotetrahydroquinaldine with a dialkyl alkoxymethylenemalonate to provide a compound of the formula

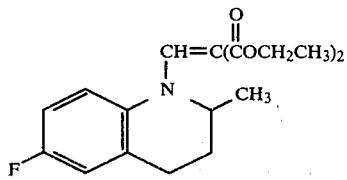

e. cyclizing the product of step (d) by heating in the presence of polyphosphoric acid followed by saponifying to provide flumequine.

2. A process for the preparation of flumequine comprising:

a. reacting 4-fluoroaniline with an alcoholic solution of crotonaldehyde in the presence of dilute aqueous acid between about 50° and 60° C. to provide a compound of the formula

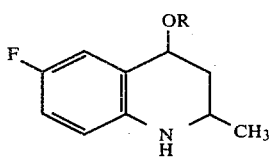

wherein R is hydrogen or alkyl having one, two, or three carbon atoms;

b. heating the product of step (a) to provide a mixture of 6-fluoroquinaldine and 6-fluorotetrahydroquinaldine as acid salts;

c. treating said acid salts with base in the presence of weak acid followed by reducing the mixture to provide 6-fluorotetrahydroquinaldine;

d. condensing said 6-fluorotetrahydroquinaldine with a dialkyl alkoxymethylenemalonate to provide a compound of the formula

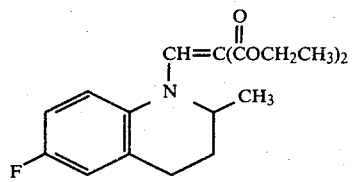

e. cyclizing the product of step (d) by heating in the presence of polyphosphoric acid followed by saponifying to provide flumequine.

3. The process according to claim 2 wherein said reactant in step (a) is a methanolic solution of crotonaldehyde and said compound provided is

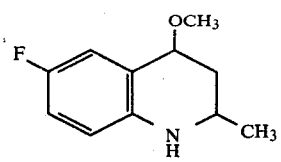

4. The process according to claim 1 wherein said dilute aqueous acid in step (a) is hydrochloric.

5. The process according to claim 1 wherein said dialkyl alkyloxymethylenemalonate of step (d) is diethylethoxymethylenealonate.

6. A process for the preparation of 6-fluorotetrahydroquinaldine comprising:

a. reacting 4-fluoroaniline with a reactant selected from the group consisting of crotonaldehyde, a precursor for crotonaldehyde which generates crotonaldehyde under acidic conditions, and an alcoholic solution of crotonaldehyde or said precursor for crotonaldehyde in the presence of dilute aqueous acid between about 50° and 60° C. to provide a compound of the formula

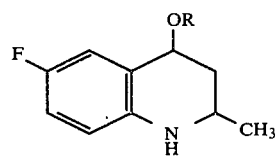

wherein R is hydrogen or alkyl having one, two or three carbon atoms;

b. heating the product of step (a) in dilute acid to provide a mixture of 6-fluoroquinaldine and 6-fluorotetrahydroquinaldine as acid salts;

c. treating said acid salts with base in the presence of weak acid followed by reducing the mixture to form 6-fluorotetrahydroquinaldine.

* * * * *

UNITED STATES PATENT AND TRADEMARK OFFICE
CERTIFICATE OF CORRECTION

PATENT NO. : 4,301,289

DATED : November 17, 1981

INVENTOR(S) : Charles M. Leir and Kirk G. Hedberg

It is certified that error appears in the above—identified patent and that said Letters Patent is hereby corrected as shown below:

Assignee: "Minnesota Mining and Manufacturing Company, Saint Paul, Minn.," should read -- Riker Laboratories, Inc., Northridge, Calif. --.

Column 1, line 27, "in vacuo" should read -- *in vacuo* --.

Column 1, line 9, "benzo-[ij]quinolizine" should read -- benzo[ij]quinolizine --.

Column 2, line 16, "following" should read -- followed --.

Column 3, line 24, "in vacuo" should read -- *in vacuo* --.

Column 4, line 43, "alone" should read -- along --.

Column 4, line 59, "in vacuo" should read -- *in vacuo* --.

line 61, "in vacuo" should read -- *in vacuo* --.

Column 5, line 4, "in vacuo" should read -- *in vacuo* --.

line 12, "in vacuo" should read -- *in vacuo* --.

Column 5, line 27, after "washed" insert -- with water --.

Column 5, line 35, "in vacuo" should read -- *in vacuo* --.

UNITED STATES PATENT AND TRADEMARK OFFICE
CERTIFICATE OF CORRECTION

PATENT NO. : 4,301,289

DATED : November 17, 1981

INVENTOR(S) : Charles M. Leir and Kirk G. Hedberg

It is certified that error appears in the above—identified patent and that said Letters Patent is hereby corrected as shown below:

Column 6, line 31, "ezeotrope" should read -- azeotrope --.

Column 8, line 28, "diethylethoxymethylenealonate" should read -- diethyl ethoxymethylenealonate --.

Signed and Sealed this

Eleventh Day of May 1982

[SEAL]

Attest:

GERALD J. MOSSINGHOFF

Attesting Officer

Commissioner of Patents and Trademarks